United States Patent [19]

Conner

[11] Patent Number: 4,613,499
[45] Date of Patent: Sep. 23, 1986

[54] SUBSTITUTED CINNAMAL DIALKYL MALONATES IN SUNSCREENING, SKIN CARE COMPOSITIONS

[75] Inventor: Donald E. Conner, Clifton, N.J.

[73] Assignee: Van Dyk & Company Inc., Belleville, N.J.

[21] Appl. No.: 747,241

[22] Filed: Jun. 21, 1985

Related U.S. Application Data

[63] Continuation-in-part of Ser. No. 600,080, Apr. 13, 1984, abandoned, which is a continuation-in-part of Ser. No. 404,964, Aug. 3, 1982, Pat. No. 4,457,911.

[51] Int. Cl.[4] .............. A61K 7/42; A61K 7/44
[52] U.S. Cl. .............................. 424/59; 424/60
[58] Field of Search ..................... 424/59, 60

[56] References Cited

U.S. PATENT DOCUMENTS

| | | | |
|---|---|---|---|
| 4,264,581 | 4/1981 | Kerkhof et al. | 424/365 |
| 4,457,911 | 8/1982 | Conner | 424/60 |

FOREIGN PATENT DOCUMENTS

| | | | |
|---|---|---|---|
| 249949 | 2/1961 | Australia | 424/60 |
| 1087902 | 8/1960 | Fed. Rep. of Germany | 424/59 |
| 2504530 | 4/1981 | France | 424/59 |

OTHER PUBLICATIONS

Chem. Abs., 1978, vol. 88, 136012e, Martelli.
Chem. Abs., 1979, vol. 90, 203363b, Rebuffat et al.

*Primary Examiner*—Dale R. Ore
*Attorney, Agent, or Firm*—Leon Chasan

[57] ABSTRACT

Compositions containing an organic sunscreen and particular substituted cinnamal dialkyl malonate adjuvants therefor are very effective in providing broad spectrum sunscreen protection and skin care.

10 Claims, No Drawings

SUBSTITUTED CINNAMAL DIALKYL MALONATES IN SUNSCREENING, SKIN CARE COMPOSITIONS

CROSS REFERENCE TO RELATED APPLICATIONS

This application is a continuation-in-part of Ser. No. 600,080 filed Apr. 13, 1984, now abandoned, which is a continuation-in-part of Ser. No. 404,964, filed Aug. 3, 1982, now U.S. Pat. No. 4,457,911.

FIELD OF THE INVENTION

Extensive studies have been made of the ultraviolet radiation of sunlight and skylight reaching the surface of the earth and the effects of such radiation on the human skin. It has been established that the radiation between 290 nanometers (nm.) and 320 nanometers produces substantially all of the burning, or erythemal energy, and a substantial portion of the tanning energy, while the between 320 nanometers and 400 nanometers promotes incident tanning. The photobiologists have divided these spectra into respectively UV-B and UV-A. The different intensities and the erythemal and tanning effectiveness of the various wave lengths within these ranges have been established and methods have been determined for calculating accurately their effects on normal untanned skin.

Approximately 76% of the physiological tanning potential of sunlight is found in the ultraviolet range between 290 nanometers and 320 nanometers, the so-called UV-B or erythema area; the balance is found in the range between 320 nanometers and 400 nanometers, the so-called UV-A tanning area.

Typical organic sunscreens such as 2-ethylhexyl para methoxy cinnamate, homomenthyl salicylate, p-aminobenzoic acid and its esters, and p-dimethyl amino benzoates, provide protection in the erythemal UV-B area, but lesser protection in the tanning area.

It is becoming increasingly apparent that ultraviolet in the tanning UV-A area can also have detrimental effects on skin health, e.g. causing premature aging, skin cancer and other adverse effects. Accordingly, the need has developed for more effective broad spectrum sunscreens to filter out the entire radiation, and to help provide total skin care.

The action of sunscreens is discussed further by Lowe "Sunscreen Predictive Assays", Cosmetics and Toiletries, pg. 65 et seq, March 1983. In that article a sun protection factor (SPF) and a correction factor (CF) are utilized:

$$SPF = \frac{\text{Correction Factor}}{\ln \sum_{290}^{320} (\% \, T \times \text{Erythemal Efficiency Spectrum} \, X \, \text{Solar Intensity Spectrum})}$$

Currently employed UVB sunscreens absorb typically in the 290–320 nm range and exhibit a λmax at approximately 310 nm when placed in a polar solvent (Isopropyl Alcohol). Most cosmetic vehicles are emulsions which contain nonpolar materials such as mineral oil. The λmax of these sunscreens in mineral oil is significantly shifted to the shorter wavelengths typically >305 nm. A UV absorber, which shows absorbance above 320 nm, is used to counteract this wavelength shift in nonpolar systems. Thus, to achieve an SPF of 15, Benzophenone-3 is conveniently employed. Because of this shift it is not possible to achieve this level of erythemal protection (SPF 15) with currently available UV absorbers by themselves in nonpolar systems. In fact even if a polar system was used, the absorber exhibits a wavelength shift due to the nonpolar skin lipids.

PRIOR ART

Some malonates have been disclosed as UV absorbers for industrial uses. Typically they are completely unsuitable for cosmetic purpose on human applications, e.g. German Patent No. 1,087,902. A malonate, diethyl p-dimethyl-amino-benzalmalonate has been disclosed in U.S. Pat. No. 3,895,104 as a conventional UV absorber in a polyamide resin film, but actually provides substantially no protection, even in the burning range.

SUMMARY OF THE INVENTION

It has now been found that certain solid, substituted, cinnamal dialkyl malonates provide minimal shift in λmax in nonpolar cosmetic oil carriers, and based on this and other characteristics, are compatible with, and adjuvants for, organic sunscreens. They thus lend themselves to the preparation of total block, skin care compositions.

DETAILED DESCRIPTION OF THE INVENTION

The adjuvants of this invention are solid, substituted, cinnamal dialkyl malonates corresponding to the formula,

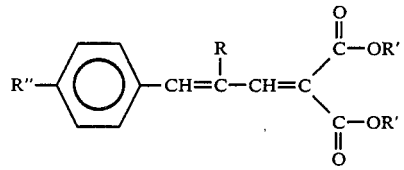

wherein R is selected from the group consisting of hydrogen and phenyl, $R^1$ is an alkyl radical having from 1 to 2 carbon atoms, and R" is selected from the group consisting of $(CH_3)_2N-$ and $CH_3-O-$.

These compounds are conveniently prepared by reacting the appropriate α-phenyl cinnamic aldehyde with a diester, such as diethyl ester, of malonic acid in a toluene solution containing 0.1 mole of piperidine acetate per mole of aldehyde. After removal of the required amount of water, the batch is washed neutral and the toluene removed under water jet vacuum and the product distilled under high vacuum.

The organic sunscreen with which the adjuvants of this invention are employed are discussed above. Cinnamal malonate can also be used as the organic sunscreen.

The overall composition adapted for application to the human skin thus comprises a cosmetic oil carrier known to the trade, e.g. mineral, vegetable and animal oils and isopropyl myristate, with an organic sunscreen, and an adjuvant of this invention. The sunscreen and the adjuvant are utilized in an amount sufficient to provide the desired protection for the skin. Typical total amounts of sunscreens and adjuvants comprise up to about 10 wt.% of the composition.

This invention, and properties of the compositions will be better understood by reference to the following examples.

EXAMPLE 1

The minimal shift in λmax for the materials of this invention is exemplified as compared to standard sunscreens.

| Standard UV Screen (Octyldimethyl PABA) | λ-max (nm) |
| --- | --- |
| Isopropyl alcohol | 310.0 |
| Mineral oil | 301.0 |

EXAMPLE 2 p-Methoxy cinnamal malonate
λmax. 351.5 nm isopropanol
λmax. 347 nm mineral oil

EXAMPLE 3 p-Dimethylamino cinnamal malonate
λmax. 373 nm isopropanol
λmax. 356 nm mineral oil

EXAMPLE 4

α-Phenyl-p-methoxy cinnamal malonate
λmax. 324.5 nm isopropanol
λmax. 319.5 nm mineral oil

EXAMPLE 5

α-phenyl-p-dimethylamino Cinnamal Malonate
λmax. 373 nm isopropanol
λmax. 356 nm mineral oil These results demonstrate that the adjuvants of this invention exhibit acceptable shifts in the UVA range as compared to standard sunscreens.

EXAMPLE 6

| Men's Moisturizer (With Sunscreen) | |
| --- | --- |
| PHASE A | 3 |
| CERASYNT WM (Emulsifier) | 7.00 |
| CERAPHYL 375 (Emollient) | 5.00 |
| EMULSYNT GDL (Emollient/Emulsifier) | 2.00 |
| ESCALOL 507 (Van Dyk) | 3.50 |
| α-phenyl-p-methoxy cinnamal malonate | 3.50 |
| (1) Spectro-Sorb | 3.00 |
| (2) Cetyl Alcohol | 1.00 |
| (3) Siloxane (SWS-03314) | 10.00 |
| (4) Brij-35 | 1.00 |
| Propylparaben | 0.10 |
| PHASE B | |
| Water, deionized | 57.95 |
| (5) Carbopol 941 | 0.25 |
| Methylparaben | 0.20 |
| (6) Germall 115 | 0.50 |
| Propylene Glycol | 5.00 |
| PHASE C | |
| NaOH (10% aq. Solution) | Q.S. |
| | 100.00% (wt.) |

(1) American Cyanamid Company
(2) Sherex Chemical
(3) SWS Silicones Corporation
(4) ICI Americas, Incorporated
(5) B. F. Goodrich Chemical Co.
(6) Sutton Labs, Inc.

PROCEDURE

In a suitable vessel, (able to contain the entire batch) weigh water, disperse carbopol and heat to 80° C. In another vessel, weigh and disperse the remaining components of Phase B and add to the batch. Weight Phase A and heat to 80° C. with agitation. When proper conditions are obtained in both Phases, add Phase A to Phase B with agitation. (Avoiding aeration) mix for 10 min. Adjust pH to 6.5 with Phase C and start cooling. Continue cooling with agitation to 28°–25° C. and package.

EXAMPLE 7

| Outdoor Facial/Hand Cream | |
| --- | --- |
| PHASE A1 | 3 |
| Water, deionized | 38.26 |
| (1) 2% Carbopol 934 Sol. | 15.00 |
| PHASE A2 | |
| Propylene Glycol | 5.00 |
| Water, deionized | 1.00 |
| Sodium Hydroxide-USP Pellets | 0.10 |
| PHASE B | |
| CERASYNT Q (Emulsifier | 2.00 |
| CERAPHYL 368 (Emollient) | 14.50 |
| ESCALOL 507 (Van Dyk) | 1.50 |
| p-methoxy cinnamal malonate | 1.50 |
| α-phenyl-p-methoxy cinnamal malonate | 1.50 |
| EMULSYNT GDL (Emollient, Emulsifier) | 2.00 |
| Cetyl Alcohol | 5.00 |
| (2) Myrj 52 | 1.00 |
| (3) Siloxane SWS 03314 | 10.00 |
| PHASE C | |
| Water, deionized | 1.00 |
| (4) Liqua Par | 0.60 |
| (5) Kathon CG | 0.04 |
| | 100.00% (wt.) |

(1) B. F. Goodrich Chemical Company
(2) ICI Americas, Incorporated
(3) SWS Silicones
(4) Mallinckrodt Chemicals
(5) Rohm and Haas Company

PROCEDURE

Weigh and combine Phase A1, heat to 80° C. and while mixing, weigh and combine Phase A2 and add to Phase A1. Weigh and combine Phase B, heat to 80° C. and mix until uniform. Slowly, add Phase B to the entire water phase. Maintain heat and agitation for 5–10 mins. and then cool. Switch to sweep agitation at 65° C. Add Phase C at 45°–50° C. and continue to mix until 30°–35° C.

The adjuvants of this invention provide surprisingly high K factors, e.g. small quantities provide very large activities.

Mixtures of the materials of this invention, and also the organic sunscreens, can be employed where desired.

The advantages of this invention will be apparent to the skilled in the art. Improved, highly effective, novel broad spectrum sunscreen compositions are made available for skin care products providing flexibility for individual needs.

It will be understood that this invention is not limited to the specific examples which have been offered as particular embodiments, and that modifications can be made without departing from the spirit thereof.

What is claimed is:

1. A sunscreening, skin care, composition adapted for application to the human skin comprising a nonpolar cosmetic oil carrier containing distributed therein an effective amount to provide substantial protection against erythemal and tanning radiation of between 320 and 400 nanometers of an organic sunscreen selected from the group consisting of 2-ethylhexyl para methoxy cinnamate, homomenthyl salicylate, cinnamal malonate, p-amino-benzoic acid and its esters, and p-dimethyl amino benzoates, and as an adjuvant therefor a substituted cinnamal dialkyl malonate corresponding to the formula,

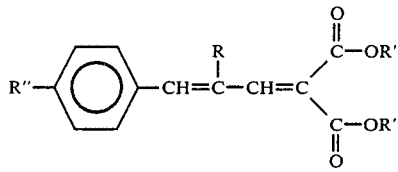

wherein R is selected from the group consisting of hydrogen and phenyl, R' is an alkyl radical having from 1 to 2 carbon atoms, and R" is selected from the group consisting of (CH$_3$)$_2$N— and CH$_3$—O—, the total amount of sunscreen and adjuvant being in the range of up to about 10 wt. of the composition.

2. The composition of claim 1 in which the adjuvant is p-methoxy cinnamal malonate.

3. The composition of claim 1 in which the adjuvant is p-dimethylamino cinnamal malonate.

4. The composition of claim 1 in which the adjuvant is α-phenyl-p-methoxy cinnamal malonate.

5. The composition of claim 1 in which the adjuvant is α-phenyl-p-dimethylamino cinnamal malonate.

6. A method of protecting the human skin from the effects of erythema and tanning radiation of between 320 and 400 nanometers in sunlight which comprises applying to said skin an effective sunscreening amount of an organic sunscreen selected from the group consisting of 2-ethylhexyl para methoxy cinnamate, homomenthyl salicylate, cinnamal malonate, p-amino-benzoic acid and its esters, and p-dimethyl amino benzoates, and as an adjuvant therefor a substituted cinnamal dialkyl malonate corresponding to the formula,

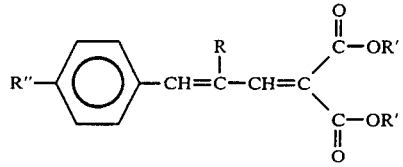

wherein R is selected from the group consisting of hydrogen and phenyl, R$^1$ is an alkyl radical having from 1 to 2 carbon atoms, and R" is selected from the group consisting of (CH$_3$)$_2$N— and CH$_3$—O—, the total amount of sunscreen and adjuvant being in the range of up to about 10 wt. of the composition.

7. The method of claim 6 in which the adjuvant is p-methoxy cinnamal malonate.

8. The method of claim 6 in which the adjuvant is p-dimethylamino cinnamal malonate.

9. The method of claim 6 in which the adjuvant is α-phenyl-p-methoxy cinnamal malonate.

10. The method of claim 6 in which the adjuvant is α-phenyl-p-dimethylamino cinnamal malonate.

* * * * *